(12) United States Patent
Ober et al.

(10) Patent No.: US 7,724,491 B2
(45) Date of Patent: May 25, 2010

(54) METHOD OF TREATING INFLAMMATION AND AUTOIMMUNE DISEASES

(75) Inventors: A. Clinton Ober, West Covina, CA (US); James L. Oschman, Dover, NH (US)

(73) Assignee: Earth FX, Inc., La Quinta, CA (US)

( * ) Notice: Subject to any disclaimer, the term of this patent is extended or adjusted under 35 U.S.C. 154(b) by 483 days.

(21) Appl. No.: 11/852,925

(22) Filed: Sep. 10, 2007

(65) Prior Publication Data

US 2008/0071232 A1    Mar. 20, 2008

Related U.S. Application Data

(60) Provisional application No. 60/825,639, filed on Sep. 14, 2006.

(51) Int. Cl.
*H01H 47/00* (2006.01)
(52) U.S. Cl. ........................................ 361/220
(58) Field of Classification Search .................. 361/220
See application file for complete search history.

(56) References Cited

U.S. PATENT DOCUMENTS

| | | | | |
|---|---|---|---|---|
| 3,781,927 A | * | 1/1974 | Zakaras | 5/616 |
| 4,321,925 A | * | 3/1982 | Hoborn et al. | 606/34 |
| 4,557,271 A | | 12/1985 | Stoller et al. | |
| 4,800,374 A | | 1/1989 | Jacobson | |
| 5,398,149 A | * | 3/1995 | Weil | 361/50 |
| 5,448,840 A | | 9/1995 | Cheskin | |
| 6,683,779 B2 | | 1/2004 | Ober | |
| 7,349,194 B2 | | 3/2008 | Elliott | |

OTHER PUBLICATIONS

Garrood TL, Lee L, and Pitzalis C, 2006; Molecular mechanisms of cell recruitment to inflammatory sites: general and tissue-specific pathways. Rheumatology 45(3):250-260.
Springer TA, 1995; Traffic signals on endothelium for lymphocyte recirculation and leukocyte emigration; Annual Reviews of Physiology 57:827-872.
Marshall BJ and Warren Jr, 1984. Unidentified curved bacilli in the stomach patients with gastritis and peptic ulceration; Lancet 1(8390):1311-1315.

(Continued)

*Primary Examiner*—Stephen W Jackson
(74) *Attorney, Agent, or Firm*—Kelly Lowry & Kelley, LLP (57) ABSTRACT

A method to speed recovery from acute injury and/or reduce and prevent chronic inflammation in an animal or human is disclosed. The method includes providing a grounded plane, conductively coupling said animal or human to the grounded plane to conduct the earth's mobile negative surface charge of free electrons from the earth to said animal or human in order to provide the body with an abundant supply of free electrons to reduce residual immune system produced reactive oxygen specie free radicals and prevent the same from oxidizing healthy tissue and exhibiting chronic inflammation in said animal or man. Applying earth's free electrons to the human body for prevention of chronic inflammation and therapeutic reduction of inflammation is described. Further described are methods to apply and maintain earth's mobile free electron charge on an animal or human while residing in modern home or work environments or in a treatment facility.

19 Claims, 1 Drawing Sheet

OTHER PUBLICATIONS

Ridker PM, Hennekens CH, Buring JE, and Rifai N, 2000; C-reactive protein and other markers of inflammation in the prediction of cardiovascular disease in women. New England Journal of Medicine 342(12):836-43.

Leu HB, Lin CP, Lin WT, Wu TC and Chen JW, 2004; Risk stratification and prognostic implication of plasma biomarkers in nondiabetic patients with stable coronary artery disease: the role of high-sensitivity C-reactive protein; Chest. 126(4):1032-9.

Ridker PM, Stampfer MJ, and Rifai N, 2001. Novel risk factors for systemic atherosclerosis: a comparison of C-reactive protein, fibrinogen, homocysteine, lipoprotein(a), and standard cholesterol screening as predictors of peripheral arterial disease; Jama 285(19):2481-2485.

Sesmilo G, Miller KK, Hayden D, and Klibanski A, 2001; Inflammatory cardiovascular risk markers in women with hypopituitarism. J Clin Endocrinol Metab. 86(12):5774-5781.

Ridker PM, Rifai N, Rose L, Buring JE, and Cook NR; 2002; Comparison of C-reactive protein and low-density lipoprotein cholesterol levels in the prediction of first cardiovascular events; New England Journal of Medicine, 347 (20):1557-65.

Algenhat FJ, and Ingber DE, 2002; Mechanotransduction: All Signals Point to Cytoskeleton, Matrix, and Integrins. Science's STKE: http://stke.sciencemag.org/cgi/content/full/OC_sigtrans;2002/119/pe6.

Pearson TA, Mensah GA, Alexander RW, et al., 2003; Markers of Inflammation and Cardiovascular Disease Application to Clinical and Public Health Practice. A Statement for Healthcare Professionals From the Centers for Disease Control and Prevention and the American Heart Association; Circulation, 107:499-511.

Knight EL, Rimm EB, Pai JK, Rexrode KM, Cannuscio CC, Manson JE, Stampfer MJ, and Curhan GC, 2004; Kidney dysfunction, inflammation, and coronary events: a prospective study; J Am Soc Nephrol, 15(7):1897-903.

Folsom AR, Chambless LE, Ballantyne CM, Coresh J, Heiss G, Wu KK, Boerwinkle E, Mosley TH Jr, Sorlie P, Diao G, and Sharrett AR, 2006; An assessment of incremental coronary risk prediction using C-reactive protein and other novel risk markers: the atherosclerosis risk in communities study; Arch Intern Med. 166 (13):1368-73.

Datta D, Ferrell WR, Sturrock RD, Jadhav ST, and Sattar N, 2006; Inflammatory suppression rapidly attenuates microvascular dysfunction in rheumatoid arthritis. Atherosclerosis 192(2):391-195.

Pleasure D, Soulika A, Singh SK, Gallo V, and Bannerman P, 2006; Inflammation in white matter: Clinical and pathophysiological aspects. Ment Retard Dev Disabil Res Rev; 12(2):141-6.

Alvarado C, Alvarez P, Puerto M, Gausseres N, Jiminez L, and De La Fuente M, 2006; Dietary supplementation with antioxidants improves functions and decreases oxidative stress of leukocytes from prematurely aging mice; Nutrition, 22(7-8):767-77.

Di Rosa M, Dell'Ombra N, Zambito AM, Malaguamera M, Nicoletti F, and Malaguarnera I, 2006; Chitotriosidase and inflammatory mediator levels in Alzheimer's disease and cerebrovascular dementia; Eur J Neurosci, 23(10):2648-56.

Weitzmann MN, and Pacifici R, 2006; Estrogen deficiency and bone loss: an inflammatory tale. Clin Invest. 116 (5):1186-94.

Isiodori AM, Giannetta E, Pozza C, Bonifacio V, and Isidori A, 2005; Androgens, cardiovascular disease and osteoporosis. J Endocrinol Invest, 28(10 Suppl):73-9.

Zilberman L, Maharshak N, Arbel Y, Rogowski O, Rozenblat M, Shapira I, Berliner S, Arber N, and Dotan I, 2006; Correlated Expression of High-Sensitivity C-Reactive Protein in Relation to Disease Activity in Inflammatory Bowel Disease: Lack of Differences between Crohn's Disease and Ulcerative Colitis, Digestion, 73 (4):205-209.

Hamminga EA, Van Der Lely AJ, Neumann HAM, and Thio HB, 2006; Chronic inflammation in psoriasis and obesity: Implications for therapy. Med Hypotheses, 67(4):768-773.

Keino H, Goto H, Mori H, Iwasaki T, and Usui M, 2006; Association between severity of inflammation in CNS and development of sunset glow fundus in Vogt-Koyanagi-Harada disease. Am J Ophthalmol, 141(6):1140-1142.

Clayton A, and Knox AJ, 2006; COX-2: A link between airway inflammation and disordered chloride secretion in cystic fibrosis?; Thorax, 61(7):552-553.

Seddon JM, George S, Rosner B, and Rifai N, 2005; Progression of age-related macular degeneration: prospective assessment of C-reactive protein, interleukin 6, and other cardiovascular biomarkers; Arch Ophthalmol, 123(6):774-82.

Ranaivo HR, Craft JM, Hu W, Guo L, Wing LK, Van Eldik LJ, and Watterson DM, 2006; Glia as a Therapeutic Target: Selective Suppression of Human Amyloid-beta-Induced Upregulation of Brain Proinflammatory Cytokine Production Attenuates Neurodegeneration; J. Neurosci, 26: 662-670.

Greten FR, Eckmann L, Greten TF, Park JM, Li ZW, Egan LJ, Kagnoff MF, and Karin M, 2004; IKKbeta links inflammation and tumorigenesis in a mouse model of colitis-associated cancer. Cell, 118(3):285-96.

Foreman J, 2006; Inflammation is Culprit in Many Ailments. On the web at: http://www.myhealthsense.com/F060403_inflamation.html.

The Secret Killer. Time Magazine, Feb. 23, 2004.

Underwood A, 2005; Quieting a body's defenses; Newsweek Special Edition on the Future of Medicine, Summer issue.

Martindale D., 2005; Reactive Reasoning: Is an inflammation protein the next cholesterol?; Scientific American, Mar. 28, 2007.

Cohen S, Kessler RC, and Gordon LU, 1995; Measuring Stress; Oxford University Press, Oxford, UK.

Halliwell B, and Gutteridge JMC, 1999; Oxygen is a toxic gas—an introduction to oxygen toxicity ad reactive oxygen species; Chapter 1 in Free Radicals in Biology and Medicine, 3rd edition, Oxford University Press, Oxford, UK.

Salpeter SR, Gregor P, Ormiston TM, Whitlock R, Rrina P, Thabane L, and Topol EJ, 2006; Meta-analysis: cardiovascular events associated with nonsteroidal anti-inflammatory drugs; Am J Med, 119(7):552-9.

Gislason GH, Jacobsen S, Rasmussen JN, Rasmussen S, Buch P, Friberg J, Schramm TK, Abilstrom SZ, Kober L, Madsen M, and Torp-Pedersen C, 2006; Risk of death or reinfarction associated with the use of selective cyclooxygenase-2 inhibitors and nonselective nonsteroidal antiinflammatory drugs after acute myocardial infarction; Circulation, 113(25):2906-2913.

Vivekanathan DP, Penn MS, Sapp SK, Hsu A, and Topol EJ, 2003; Use of antioxidant vitamins for the prevention of cardiovascular disease: meta-analysis of randomised trials; Lancet, 361: 2017-23.

Ben-Mahmud BM, Chan WH, Abdulahad RM, Datti A, Orlacchio A, Kohner EM, and Chibber R, 2006; Clinical validation of a link between TNF-alpha and the glycosylation enzyme core 2 GlcNAc-T and the relationship of this link to diabetic retinopathy. Diabetologia, 49(9):2185-2191.

Anisimov S.V., Mareev E.A., and Bakastov S.S.; On the generation and evolution of aeroelectric structures in the surface layer. Journal of Geophysical Research, vol. 104, No. D12, pp. 14,359-14,367, Jun. 27, 1999.

Applewhite Roger, The Effectiveness of a Conductive Patch and a Conductive Bed Pad in Reducing Induced Human Body Voltage Via the Application of Earth Ground, Static Prevention, Inc., Anaheim, California, Apr. 29, 2004.

Chevalier Gaetan, Mori Kazuhito, and Oschman James L., The effect of earthing (grounding) on human physiology.

Ghaly Maurice, and Teplitz Dale; The Biologic effects of grounding the human body during sleep, as measured by cortisol levels and subjective reporting of sleep, pain and stress.

Geophysics Study Committee, Studies in Geophysics: The Earth's Electrical Environment, National Academy Press, Washington, D.C. 1986.

Leu Hsin-Band, Lin Chih-Pei, Lin Wen-Tasi, Wu Tao-Cheng and Chen Jaw-Wen, Risk Stratification and Prognostic Implication of plasma Biomarkers in Nondiabetic Patients With Stable Coronary Artery Disease: The Role of High-Sensitivity C-Reactive Protein, Chest, The Cardiopulmonary and Critical Care Journal, American College of Chest Physicians, Northbrook, Illinois, Sep. 2, 2006.

Normark Staffan, The Nobel Prize in Physiology or Medicine 2005 Presentation Speech, Karolinska Institutet, Stockholm, Dec. 10, 2005.

Minkoff David I., Best Cases in Biological Medicine, Explore! vol. 13, Nov. 6, 2004.
Ober A. Clinton, Grounding the Human Body to Neutralize Bio-Electrical Stress from Static Electricity and EMFs., ESD Journal, Feb. 22, 2004.
Szent-Gyorgyi, Towards a New Biochemistry?; Science, pp. 609-611, Jun. 27, 1941.

Szent-Gyorgi, The Study of Energy-levels in Biochemistry, Nature, pp. 157-159, Aug. 9, 1941.
Norden Bengt, The Nobel Prize in Chemistry 1999, Presentation Speech, Stockholm, Dec. 10, 1999.

* cited by examiner

FIG. 1

METHOD OF TREATING INFLAMMATION AND AUTOIMMUNE DISEASES

BACKGROUND OF THE INVENTION

The present invention resides in a method to reduce and prevent inflammation and to treat inflammation related autoimmune disorders. More particularly, the present invention relates to a method of inhibiting the expression of chronic inflammation in an animal or human by conductively coupling the body with the earth to conduct earth's mobile surface charge of free electrons from the earth to the body in order to restore the body's natural supply of free electrons and thereby reduce and prevent residual immune system-produced reactive oxygen species (ROS) free radicals from oxidizing normal tissue. When an animal or human body is naturally charged with earth's mobile free electrons, residual immune system-produced free radicals have a readily available source of free electrons to rapidly reduce their oxidative state. This inhibits free radical oxidation of healthy tissue and thereby speeds recovery from acute injury and inhibits the promotion and manifestation of chronic inflammation and inflammation related health disorders. Free electrons from the earth do not interfere with the normal and vital immune responses to tissue damage and/or infection and subsequent tissue repair processes; instead, electrons have a natural protective effect on healthy or undamaged cells and tissues near a site of trauma. In other words, free electrons from the earth augment and focus the body's natural responses to injury.

It is well established, though not widely known, that the surface of the earth possesses a limitless and continuously renewed supply of free or mobile electrons. The earth's surface is electrically conductive and is maintained at a negative potential by the global atmospheric electrical circuit. The universal conductivity of the earth's surface varies somewhat from place to place, depending upon water and mineral content, vegetation and other factors. However, these factors have relatively little effect on the ability of an earth connection to allow free electrons to flow from the earth to the body or vice versa. Further, any conductive object, coupled with the earth, will conduct earth's mobile charge of free electrons and equalize with it and thereafter maintain the negative potential of the earth. Human and animal bodies are conductive and when they are coupled with the earth they also conduct and become saturated with the earth's mobile electrons. Humans and animals and their respective progenitors lived in conductive (barefoot) contact with the earth during their primary evolutionary period. The body's reactive oxygen species immune response mechanisms also developed during this period when humans and animals lived in a natural grounded state. The inventor has linked loss of natural grounding via the integration of plastic and other insulative materials in our living environments as a contributor to the rapid rise in chronic inflammation and related health disorders. Non-conductive natural and artificial polymer-based soled footwear, floor coverings, bedding and the like now insulate most humans and domestic animals from routine conductive contact with the earth. Clinical case studies (Amalu, William, DC, DABCT, FIACT; *Medical Thermography Case Studies*) document that when the body is conductively coupled with the earth, acute injuries and chronic inflammation and related health disorders resolve naturally.

The primary defence mechanism of the body is the release of reactive oxygen specie (ROS) free radicals by the immune system. The immune system's ROS response is triggered by injury or disease. White blood cells are constantly circulating within the tissues, essentially poised to respond to the presence of viruses, bacteria or injured cells (Garrood T L Lee L Pitzalis C, 2006; *Molecular mechanisms of cell recruitment to inflammatory sites: general and tissue-specific pathways*; Rheumatology 45(3):250-260). When an injury occurs, chemical, electrical and other messages are produced that attract white blood cells to the injured or diseased tissue. Chemical signals from the injured tissue can attract other, more specialized cells (Springer T A, 1995; *Traffic signals on endothelium for lymphocyte recirculation and leukocyte emigration*; Annual Reviews of Physiology 57:827-872). Inflammation increases blood flow to an area, producing redness and warmth.

Part of the inflammatory response involves various immune cells, known as neutrophils, as well as other types of phagocytes, which secrete an abundance of powerful oxidizing agents (free radicals) in a process known as the respiratory burst. The respiratory burst consists of a complex mix of very reactive molecules such as hydrogen peroxide, oxidized halogens, chloramines and oxidizing radicals such as hydroxyl radical, ⁻OH, that aid in the destruction of invading microorganisms. To restore their electrical neutrality, these agents tear electrons from the structures of invading organisms and damaged cells, rapidly destroying them. While these highly reactive substances are manufactured for use at specific sites of infection or tissue damage, they can leak into surrounding tissues, where they inflict various types of undesirable but unavoidable damaging side effects.

While ROS free radicals are obviously vital to the immune response, problems arise when the process does not completely wind down after an injury or site of disease has been cleared of pathogens and cellular debris. Under these conditions, residual ROS free radicals continue to attack and oxidize healthy tissue. This oxidation of healthy tissue then leads to the release of additional chemical signals that re-stimulate the immune system. The immune system responds by delivering more ROS free radicals, establishing a destructive or vicious cycle that can continue indefinitely, even for dozens of years. Some biomedical researchers refer to this as silent inflammation, and it is being recognized as the culprit behind almost every modern chronic disease.

Scientists have known for a long time that the inflammatory response can backfire, causing a host of autoimmune diseases. There about 80 such disorders, the most common being rheumatoid arthritis, multiple sclerosis, Hashimoto's thyroiditis, Graves' disease, Lupus, and Crohn's disease.

The idea that chronic inflammation could be involved in disease began to gain credence when doctors realized that stomach ulcers were not caused by stress or spicy food, but by inflammation triggered during bacterial infection (Marshall B J Warren J R, 1984; *Unidentified curved bacilli in the stomach of patients with gastritis and peptic ulceration*; Lancet 1(8390):1311-1315; also see the 2005 Nobel Prize for Physiology or Medicine awarded jointly to Barry J. Marshall and J. Robin Warren for their discovery of "the bacterium *Helicobacter pylori* and its role in gastritis and peptic ulcer disease.")

It has also long been known that Type 1 diabetes is linked to inflammation—the body's immune system attacks the cells that make insulin. New research is suggesting that Type 2 diabetes, the kind that generally occurs in adulthood, often begins with insulin resistance, in which cells stop responding properly to insulin. Doctors now know that during chronic inflammation, one of the chemicals released is tumor necrosis factor (TNF), which makes cells more resistant to insulin. The TNF connection also helps explain why obesity, particularly abdominal obesity, leads to diabetes. Fat cells used to be thought of as storage depots for energy, as metabolically inactive; now we know that fat cells are little hotbeds of inflammation—excess fat in the belly is a source of inflammation.

Recently evidence has accumulated to show that inflammation is a major factor in far more conditions than the autoimmune diseases, ulcers and diabetes. Some of the most thorough documentation of the role of inflammation in disease has come from research of Dr. P M Ridker and his colleagues at the Center for Cardiovascular Disease Prevention, and Division of Cardiology, Brigham and Women's Hospital and Harvard Medical School in Boston, Mass., USA (Ridker P M Hennekens C H, Buring J E, and Rifai N, 2000; *C-reactive protein and other markers of inflammation in the prediction of cardiovascular disease in women*; New England Journal of Medicine, 342(12):836-43). Suspecting that inflammation is involved in the pathogenesis of cardiovascular events, these researchers measured the levels of markers of inflammation in a prospective controlled study among 28,263 apparently healthy postmenopausal women over a mean follow-up period of three years. They assessed the risk of cardiovascular events associated with a variety of established inflammatory markers, including high-sensitivity C-reactive protein (hs-CRP), homocysteine and a variety of lipid (e.g. cholesterol) and lipoprotein measurements. Cardiovascular events were defined as death from coronary heart disease, nonfatal myocardial infarction or stroke, or the need for coronary revascularization procedures. Of 12 markers measured, hs-CRP proved to be the strongest predictor of the risk of cardiovascular events. Markers of inflammation, when combined with lipid measurements, were significantly better at predicting risk than models based on lipid levels alone ($P<0.001$). The levels of hs-CRP and serum amyloid A were significant predictors of risk even in the subgroup of women with normal cholesterol levels. The study concluded that adding the measurement of the inflammatory marker, C-reactive protein, to screening based on lipid levels could improve the identification of persons at risk for cardiovascular events. In 2004, a group in Taipei, Taiwan essentially confirmed these results in a study of non-diabetic patients (Leu H B, Lin C P, Lin W T, Wu T C, and Chen J W, 2004; *Risk stratification and prognostic implication of plasma biomarkers in nondiabetic patients with stable coronary artery disease: the role of high-sensitivity C-reactive protein*; Chest, 126(4):1032-9).

In 2001, Ridker and colleagues studied the risk factors for systemic atherosclerosis in 14,916 initially healthy US male physicians. Again, total cholesterol-HDL-C ratio and CRP were the strongest independent predictors of development of peripheral arterial disease (Ridker P M, Stampfer M J, and Rifai N, 2001; *Novel risk factors for systemic atherosclerosis: a comparison of C-reactive protein, fibrinogen, homocysteine, lipoprotein(a), and standard cholesterol screening as predictors of peripheral arterial disease*; JAMA, 285(19): 2481-2485).

In 2001, another group at Massachusetts General Hospital and Harvard Medical School, Boston, Mass. USA reported on high levels of CRP associated with hypopituitarism and growth hormone deficiency. This phenomenon had already been reported in men, and this study extended the findings to women. Hypopituitary women have increased levels of IL-6 and CRP, both of which are inflammatory markers of atherosclerosis (Sesmilo G, Miller K K, Hayden D, and Klibanski A, 2001; *Inflammatory cardiovascular risk markers in women with hypopituitarism*; J Clin Endocrinol Metab., 86 (12): 5774-5781).

In 2002, Ridker and colleagues reported measurements of C-reactive protein and LDL cholesterol in 27,939 apparently healthy American women who were then followed for a mean of eight years for the occurrence of myocardial infarction, ischemic stroke, coronary revascularization, or death from cardiovascular causes. They found that base-line levels of each marker had a strong linear relation with the incidence of cardiovascular events.

Further study by Ridker and colleagues revealed a correlation between chronic inflammation and sudden cardiac death (Alenghat F J, and Ingber D E, 2002; *Mechanotransduction: All Signals Point to Cytoskeleton, Matrix, and Integrins; Science's STKE*; http://stke.sciencemag.org/cgi/content/full/OC_sigtrans;2002/119/pe6).

As a result of these studies, and others like them, the American Heart Association and the Centers for Disease Control and Prevention recommended in 2003 that doctors include a test for free radicals in their medical check-ups, to determine a patient's risk for heart disease (Pearson T A, Mensah G A, Alexander R W, et al.; 2003; *Markers of Inflammation and Cardiovascular Disease Application to Clinical and Public Health Practice. A Statement for Healthcare Professionals From the Centers for Disease Control and Prevention and the American Heart Association*; Circulation 107: 499-511). Subsequently there has been a veritable explosion of research into the association of inflammation and inflammatory markers with a wide range of chronic illnesses. Today, nearly every branch of medicine and surgery includes the study of inflammation (Alenghat F J, supra.)

Inflammation is now thought to be the underlying mechanism of more than 80 chronic illnesses, in addition to the autoimmune disorders mentioned above. These chronic illnesses involve almost every human organ system. They include diseases of the nervous, gastrointestinal, endocrine and respiratory systems as well as the skin and connective tissues. In all of these diseases, the underlying problem is similar—the body's immune system is attacking the very organs it was designed to protect. And inflammation in one organ can be associated with problems in other organs.

For example, in 2004, Knight and colleagues studied the association among kidney function, inflammatory biomarker levels, and coronary events. A total of 244 women with no history of cardiovascular disease that subsequently had incident coronary events were matched to 486 control subjects. High-sensitivity CRP (hs-CRP), IL-6, and sTNFR I and II levels were all significantly associated with an increased odds of coronary events in women with reduced kidney function but not in women with normal kidney function. Kidney dysfunction is associated with an increased odds of coronary events, and inflammation, as assessed by higher inflammatory biomarker levels, specifically hs-CRP, IL-6, and soluble tumor necrosis factor receptor I and II were significantly associated with coronary events only in women with reduced kidney function (Knight E L, Rimm E B, Pai J K, Rexrode K M, Cannuscio C C, Manson J E, Stampfer M J, and Curhan G C, 2004; *Kidney dysfunction, inflammation, and coronary events: a prospective study*; J Am Soc Nephrol, 15(7):1897-903).

Subsequent ongoing research has confirmed a role for inflammation in atherosclerosis (Folsom A R, Chambless L E, Ballantyne C M, Coresh J, Heiss G, Wu K K, Boerwinkle E, Mosley T H, Jr, Sorlie P, Diao G, and Sharrett A R, 2006; *An assessment of incremental coronary risk prediction using C-reactive protein and other novel risk markers: the atherosclerosis risk in communities study*; Arch Intern Med. 166 (13):1368-73), diabetes (Ben-Mahmud B M, Chan W H, Abdulahad R M, Datti A, Orlacchio A, Kohner E M, and Chibber R, 2006; *Clinical validation of a link between TNF-alpha and the glycosylation enzyme core 2 GlcNAc-T and the relationship of this link to diabetic retinopathy*; Diabetologia, 49(9):2185-2191), rheumatoid arthritis (Datta D, Ferrell W R, Sturrock R D, Jadhav S T, and Sattar N, 2007; *Inflammatory suppression rapidly attenuates microvascular dysfunction in rheumatoid arthritis*; Atherosclerosis, 192(2):391-195), multiple sclerosis (Pleasure D, Soulika A, Singh S K, Gallo V, and Bannerman P, 2006; *Inflammation in white matter: Clinical and pathophysiological aspects*; Ment Retard Dev Disabil Res Rev. 12(2):141-6), aging (Alvarado C, Alvarez P, Puerto M, Gausseres N, Jimenez L, and De la Fuente M, 2006; *Dietary supplementation with antioxidants improves functions and decreases oxidative stress of leukocytes from prematurely aging mice*; Nutrition, 22(7-8):767-77), Alzheimer's disease (Di Rosa M, Dell'Ombra N, Zambito A M, Malaguarnera M, Nicoletti F, and Malaguarnera I, 2006; *Chitotriosidase and inflammatory mediator levels in Alzheimer's disease and cerebrovascular dementia*; Eur J Neurosci, 23(10):2648-56), osteoporosis (Weitzmann M N, and Pacifici R, 2006; *Estrogen deficiency and bone loss: an inflammatory tale*; Clin Invest. 116(5):1186-94), asthma (Isidori A M, Giannetta E, Pozza C, Bonifacio V, and Isidori A, 2005; *Androgens, cardiovascular disease and osteoporosis*; J Endocrinol Invest. 28(10 Suppl):73-9), bowel disorders (Zilberman L, Maharshak N, Arbel Y, Rogowski O, Rozenblat M, Shapira I, Berliner S, Arber N, and Dotan I, 2006; *Correlated Expression of High-Sensitivity C-Reactive Protein in Relation to Disease Activity in Inflammatory Bowel Disease: Lack of Differences between Crohn's Disease and Ulcerative Colitis*; Digestion, 73(4):205-209), psoriasis (Hamming a E A, van der Lely A J, Neumann H A, and Thio H B, 2006; *Chronic inflammation in psoriasis and obesity: Implications for therapy*; Med Hypotheses, 67(4):768-773), meningitis (Keino H, Goto H, Mori H, Iwasaki T, and Usui M, 2006; *Association between severity of inflammation in CNS and development of sunset glow fundus in Vogt-Koyanagi-Harada disease*; Am J. Opthalmol. 141(6):1140-1142), cystic fibrosis (Clayton A, and Knox A J, 2006; *COX-2: a link between airway inflammation and disordered chloride secretion in cystic fibrosis?*; Thorax, 61(7):552-553), age related macular degeneration (Seddon J M, George S, Rosner B, and Rifai N, 2005; *Progression of age-related macular degeneration: prospective assessment of C-reactive protein, interleukin 6, and other cardiovascular biomarkers*; Arch Opthalmol, 123(6):774-82), and cancer (Allgayer H, and Kruis W, 2006; *From chronic inflammation to metastasing colon cancer—the endless story of the NSAIDs*; Z Gastroenterol, 44(7):611-613). The individual references for the previous sentence are drawn from recent literature to show that studies of this kind are currently one of the most active areas in clinical biomedicine.

The details of these phenomena are being worked out. For example, in neurodegenerative diseases such as Alzheimer's, it has been found that whenever the brain is injured or infected, glial cells in the brain secrete cytokines. Normally, this response shuts down when the injury or infection is over. But in chronic neurodegenerative diseases like Alzheimer's, these glial cells are activated too high or too long or both. The plaques and tangles in patients' brains attract the attention of glial cells, making them secrete even more cytokines to try to repair this damage, and creating chronic inflammation (Ranaivo H R Craft J M Hu W Guo L Wing L K, Van Eldik L J, and Watterson D M, 2006; *Glia as a Therapeutic Target: Selective Suppression of Human Amyloid-beta-Induced Upregulation of Brain Proinflammatory Cytokine Production Attenuates Neurodegeneration*; J. Neurosci, 26: 662-670).

The role of inflammation in cancer development is under active investigation. It has been discovered that recurrent inflammation and chronic infections actually contribute to a large number of different types of cancers. Tumors arise from chronic inflammation that acts together with chemical carcinogens. A relationship between cancer and inflammation due to chronic infection has been suspected, but not proven, for many years. In a 1986 study, for example, one researcher compared the inflammatory response to a wound healing response, saying tumors were wounds that do not heal. The recent findings establish a role of myeloid cells in inflammation-associated tumor promotion in addition to their role in tumor progression and invasiveness (Greten F R, Eckmann L, Greten T F, Park J M, Li Z W, Egan L J, Kagnoff M F, and Karin M, 2004; *IKKbeta links inflammation and tumorigenesis in a mouse model of colitis-associated cancer*; Cell, 118(3):285-96).

Modern research is confirming that inflammatory diseases are virtually epidemic and include some of the most devastating afflictions of our times. Over the evolutionary eons, "we developed these important host defenses to let us get to reproductive age," said Dr. Peter Libby, chief of cardiovascular medicine at Brigham and Women's Hospital in Boston. "Now, the lifespan has almost doubled, and these same [immune responses] contribute to diseases in the end." Chronic inflammation is so similar in different diseases, Libby said, that when he lectures, he uses many of the same slides, whether he's talking about diseases of the heart, kidneys, joints, lung or other tissues (Foreman J, 2006; *Inflammation is Culprit in Many Ailments*; On the web at: http://www.myhealthsense.com/F060403_inflamation.html.). In "The Inflammation Cure," J. Meggs, MD states that, "Inflammation may turn out to be the elusive Holy Grail of medicine— the single phenomenon that holds the key to sickness and health." (Meggs W J, and Svec C, 2003; *The Inflammation Cure: How to Combat the Hidden Factor Behind Heart Disease, Arthritis, Asthma, Diabetes, & Other Diseases*; McGraw-Hill, New York). Everybody knows someone suffering from an inflammation disease. Many physicians, scientists, and patients wonder what has caused inflammation to become so common.

These observations and conclusions further relate significantly to the roles of inflammation and ROS free radicals in chronic disease that have been incorporated into an important new theory that has steadily been gaining support within the medical community. The new theory states that the immune reaction generally known as inflammation may be the underlying cause of a wide range of chronic diseases.

As a consequence of current research on inflammation, Time Magazine Newsweek and Scientific American have recently reported that inflammation is emerging as the "Alpha and Omega of disease" . . . that reducing inflammation is the most important thing a person can do to restore their health and prevent disease (The Secret Killer. Time Magazine; Feb. 23, 2004); (Underwood A, 2005, *Quieting a body's defenses*; Summer issue); (Martindale D, 2005; *Reactive Reasoning: Is an inflammation protein the next cholesterol?*; Scientific American.com, March 28 issue).

The familiar manifestations of inflammation should be short lived: swelling, redness, decreased range of motion, heat and pain. However, when the inflammatory response does not shut down properly, inflammation can persist, causing the disruptive manifestations listed in the previous sentence to linger. The resulting discomfort and unnecessary damage to tissues stress the body, prevent proper rest and recovery, and give rise to a host of stress-related disorders (Cohen S, Kessler R C, and Gordon L U, 1995; Strategies for measuring stress in studies of psychiatric and physical disorders. Ch. 1, pp. 3-26 in *Measuring Stress*; Oxford University Press, Oxford, UK) as well as a long list of other problems.

Those other problems, known by a variety of disease names, are being recognized as having a common denominator—chronic inflammation.

These problems are particularly significant for the athlete or performer or other person involved in strenuous exertion or physical exercise. The reason for this is that vigorous exertion can increase oxygen intake by a factor of 10 to 20 times. This in turn results in a condition called hyperoxia (elevated oxygen tension in the tissues). Oxygen is a highly reactive and toxic substance (Halliwell B, and Gutteridge J M C, 1999; *Oxygen is a toxic gas—an introduction to oxygen toxicity and reactive oxygen species*; Chapter 1 in Free Radicals in Biology and Medicine, 3rd edition, Oxford University Press, Oxford, UK), and excess oxygen in the tissues leads to increased intracellular production of oxygen-derived free radicals to levels that can exceed the capacity of the antioxidant defenses that normally remove oxidants. When this happens, free radical damage can overwhelm the restorative processes that normally repair cells and cellular components including DNA. When extreme exertion is coupled with injury, as often occurs in highly competitive sports, the result can be an even larger build-up of free radical damage that can severely inhibit and thereby prolong the recovery process.

The inflammation theory of disease has triggered the search for new anti-inflammatory compounds and other methods for neutralizing excess free radicals. Cortisone was the first steroid drug available. In 1935, researchers at Mayo Clinic, Rochester, Minn., isolated the hormone cortisone from adrenal glands. In 1948, doctors first used the new drug to treat a 28-year-old woman with severe rheumatoid arthritis. Cortisone remarkably relieved her inflamed, swollen joints after just a few days of use. People who normally couldn't climb out of bed or into a bathtub could do so after using the drug. For a long period of time, cortisone injections, also known as cortisol or corticosteroid injections were widely used for reducing pain associated with inflammation. But these drugs do not assist in the healing process. In fact, cortisone has actually been shown to slow healing. This is a central problem in sports medicine. The injured performer gets immediate pain relief from the treatment and is able to continue his or her activity, but this can lead to more serious problems in the longer term.

Because of problems with its side effects, the use of cortisol and related drugs has been largely supplanted with non-steroidal anti-inflammatory compounds (NSAIDS), which are available both by prescription and over-the-counter. As with cortisol, however, experience is showing that prolonged use of NSAIDS can also lead to serious side effects. For example, people who have survived a first heart attack have a higher risk of dying or having a second heart attack if they are taking non-steroidal anti-inflammatory drugs (NSAIDs), including the newer class called cox-2 inhibitors (Salpeter S R Gregor P Ormiston T M Whitlock R, Raina P, Thabane L, and Topol E J, 2006; *Meta-analysis: cardiovascular events associated with nonsteroidal anti-inflammatory drugs*; Am J. Med. 119 (7):552-9; Gislason G H, Jacobsen S, Rasmussen J N, Rasmussen S, Buch P, Friberg J, Schramm T K, Abildstrom S Z, Kober L, Madsen M, and Torp-Pedersen C; 2006; *Risk of death or reinfarction associated with the use of selective cyclooxygenase-2 inhibitors and nonselective nonsteroidal antiinflammatory drugs after acute myocardial infarction*; Circulation. 113(25):2906-2913).

Many people have turned to vitamins and nutritional supplements thought to have antioxidant and anti-inflammatory properties, but there is debate about the effectiveness of these substances (Vivekananthan D P, Penn M S, Sapp S K, Hsu A, and Topol E J, 2003; *Use of antioxidant vitamins for the prevention of cardiovascular disease: meta-analysis of randomised trials; Lancet* 361: 2017-23).

In spite of these difficulties, it is obviously important to develop means to reduce free radical concentrations in tissues, and a variety of chemical methods continue to be disclosed to accomplish this. These methods have the disadvantage that once the antioxidant chemical has reduced a free radical by donating an electron to it, the antioxidant itself can become a free radical. The resulting charge imbalance can be passed in a series of reactions from molecule to molecule, causing further oxidative stress and disrupting metabolism. In addition, the antioxidant, once it has served its purpose, must be metabolized and excreted from the organism, posing an additional work load on the biochemical machinery of the body. Moreover, antioxidants and their metabolites can have deleterious side effects.

The many disadvantages to the prior art related to chemical control of the acute and chronic phases of inflammation are overcome in this invention, which provides direct conductive pathways for natural antioxidant electrons from the earth to rapidly reach sites of inflammation in the body.

There are two ways of describing phenomena that cannot be seen directly, such as electricity. The metallic wire in which electrons flow to an appliance, such as a light bulb, can be visualized as being composed of atoms that are more or less rigid and generally held in their positions like the atoms in a crystal. Through this rigid atomic matrix flows an electric current that can be visualized as a flow of particles called electrons that more or less resemble billiard-balls. A closer look reveals them as free electrons, because they are not held in place. None of these conduction electrons belongs to any particular atom in the lattice. In other words, the atoms are not localized, (the physics term is that they are "delocalized") and are free to move when a force such as a voltage is exerted upon them. The free electrons can be described as a sort of electric fluid, or as a cloud, or as a gas. Physicists have used all of these terms: billiard balls, delocalized electrons, fluid or quantum fluid, cloud, and gas to describe conduction electrons. The classical way of viewing this, the Newtonian model, is a mechanical perspective in which the billiard balls are discrete and localizable entities that have properties like velocity and acceleration and momentum and move when they are pushed.

Quantum physics teaches us that there is another way of looking at the situation. Yes, if you look at the electrons in a certain way, they behave as particles. But if you look at them in a different way, they behave as waves.

In the early years of the $20^{th}$ Century, physicists were struggling to rationalize the two seemingly different perspectives on the electron: is it a particle or is it a wave? This came to be known as the wave-particle duality Different measurements made on a system reveal it to have either particle-like or wave-like properties. The Danish physicist, Niels Bohr, contributed the important concept of complementarity: the wave and the particle perspectives are not mutually exclusive but are complementary: you cannot really understand electrons or atoms without considering both perspectives.

Complementarity emerged as a basic principle of quantum theory. Bohr, in collaboration with Heisenberg, used complementarity as a philosophical adjunct to the recently developed mathematics of quantum mechanics and in particular to the Heisenberg uncertainty principle. The uncertainty principle states that a single quantum mechanical entity can either behave as a particle or as wave, but never simultaneously as both; that a stronger manifestation of the particle nature leads to a weaker manifestation of the wave nature and vice versa.

A premise of this invention is that electrons are abundantly available from the surface of the earth and that these electrons can be conducted via the bare feet or other parts of the skin surface to the body surface and into the body to neutralize free radicals in tissues throughout said body.

As with any other phenomenon in nature, there are complementary ways of discussing the process. As with the wave-particle duality, the different ways of viewing the phenomenon are not mutually exclusive, but must be taken together to find the most accurate way of saying how nature is working in this situation.

A major challenge is extending understandings at the quantum or microscopic level to larger scale or macroscopic phenomena. This is an important endeavor in relation to medicine as well as this patent because cells, tissues, organs and organisms function and behave at observable millimeter to centimeter or larger length scales, but the events creating and governing such behaviors occur on the subatomic and atomic scales measured at Angstrom and micron scales. Atoms and molecules described as free radicals are sandwiched between the microscopic and macroscopic levels. The challenge is to apply sophisticated quantum or microscopic understandings to macroscopic behavior. Much confusion arises when trying to stretch subjective understandings of the behavior of the visible or macroscopic world to events that are occurring at invisible electronic or quantum levels and that are therefore more precisely explainable by the physics that has been developed to explain events taking place at those small scales. For example, one observes that when one throws a light switch, electricity flows to the light and it begins to glow. To use this as an analogy of how electrons move through the surface of the earth or within living systems introduces considerable confusion and lack of clarity, as the behaviors of electrons and electric currents are invisible, and neither the earth's crust nor living tissues behave like simple metallic wires. It is a central issue in modern biomedicine to bring to modern medical theory and practice the great discoveries of quantum mechanics, which have been awarded a series of Nobel Prizes over the last century.

The terms, microscopic and macroscopic are not exactly defined. A common perspective is that microscopic refers to objects and processes taking place at roughly atomic dimensions or smaller, while macroscopic refers to systems that are large enough to be visible in the ordinary sense. A more exact definition references the number of particles in a system. A system is macroscopic if conventional statistics can be applied to it with reasonable accuracy. For instance, if it is necessary to keep the statistical error below one percent, a macroscopic system would have to contain more than about ten thousand particles. Any system containing less than this number of particles would be regarded as microscopic, and, hence, conventional statistics could not be applied without unacceptable error. In this case, one would have to shift to a branch of physics known as quantum statistical mechanics.

The explanation of the phenomena involved in this patent begins with the more familiar models of electronic conduction, and then looks more closely, using the microscopic picture that has been developed by quantum physics.

It is accepted that the earth's surface is electrically conductive and is maintained at a negative potential by a global electrical circuit (Williams E R and Heckman S J, 1993; *The local diurnal variation of cloud electrification and the global diurnal variation of negative charge on the earth*; Journal of Geophysical Research, Volume 98:5221-5234; Anisimov S V, Mareev E A, and Bakastov S S, 1999; *On the generation and evolution of aeroelectric structures in the surface layer*; J Geophys Res 104: (D12) 14359-14367). It is also accepted that there are three main generators in the global electric circuit: the solar wind entering the magnetosphere; the ionospheric wind; and thunderstorms (Volland H, 1984, *Atmospheric electrodynamics*; In: *Physics and Chemistry in Space*, edited by Lanzerotte L J, Berlin; Springer-Verlag; Williams E R and Heckman S J, supra).

An estimated 1000 to 2000 thunderstorms are continually active around the globe, emitting thousands of lightening strikes per minute. This creates a constant current of thousands of amperes transferring positive charge to the upper atmosphere and negative charge to the surface of the earth. The earth's surface is therefore an abundant source of free electrons (Geophysics Study Committee, 1986, *The Earth's electrical environment*; Technical Report. Washington, D.C.: National Academy Press).

In addition to the above mentioned solar and atmospheric sources of electrons, the earth's molten core may participate because of its metallic iron-nickel content that is maintained at high pressure and temperature, conditions known to produce free electrons in molten metals.

Those familiar with the arts in the fields of electrophysiology and biomedical instrumentation will be aware that multiple conductive pathways exist between internal organs and the body skin surface, and vice versa. This is the basis for familiar clinical diagnostic tools such as the electrocardiogram, electroencephalogram, and electromyogram, for example. In these examples, electrical activities produced by the activities of the heart, neurons in the brain, and muscles, respectively, follow conductive pathways to the skin surface where they can be conductively coupled via electrode patches and leads to appropriate measuring instruments. The conventional arrangement of electrodes for recording the standard electrocardiogram involves placing electrodes on the two wrists and left ankle, although many other arrangements have been used for specific purposes. That these conductive pathways work in reverse, from the skin surface to the organs within the body, is likewise well known. Electrical stimulation of the skin to affect the heart underlies cardiac pacing and defibrillation, for example. Likewise, electrical stimulation of the brain via electrodes on the scalp, in a method known as DC brain polarization, is being researched for effects on cognition and other aspects of brain function. Finally, it has been known since 1867 that electrical stimulation at particular points on the skin surface can activate particular muscles. These discoveries and related methods, such as electroacupuncture, document the presence of conductive pathways from the skin surface to the tissues and organs throughout the body.

A deeper and more holistic understanding of the conduction of free electrons in the earth and in the human body arises from consideration of the physics of electrons and electron conduction in various forms of matter. The study of electrons and electron conduction belongs to the largest area of contemporary physics known as condensed matter physics (formerly referred to as solid state physics, which is now considered to be one branch of condensed matter physics).

The free electron model contrasts with the tight-binding model, which treats the properties of the electrons that are tightly bound or localized in the individual atomic cores or nuclei of the matter in which they are found. A conductive material such as a metal can have both free or mobile electrons and tightly bound or immobile electrons. A semiconductor is a material with electrical conductivity that is intermediate between that of an insulator and a conductor. More importantly, a semiconductors' conductivity may be modified by introducing impurities in a process known as doping. The ability to control conductivity in small and well-defined regions of semiconductor material has led to the development of a broad array of miniaturized electronic devices that have become the basis for nearly all modern electronics. This is mentioned because most if not all biomolecules have semiconductor properties.

An electrical conductor is defined as a material containing movable charges of electricity; electricity is a general term for a variety of phenomena resulting from the presence and flow of electric charge; electric charge is defined as a fundamental property of some subatomic particles which determines their electromagnetic interactions.

Physicists refer to free electrons as being present as a "cloud" or "gas" composed of mobile electrons in a material such as a crystal or a metal. There are two basic models for the conduction of free electrons, the Drude model of electrical conduction, and the Drude-Sommerfeld model. Both of these models neglect Coulombic or electrostatic electron-electron interactions and assume limited interactions between the free electrons and the more localized electrons and protons in the solid matrix in which they exist.

The Drude model is based on classical or Newtonian physics and kinetic theory. The kinetic approach assumes that a material contains both immobile positive ions (protons) and mobile electrons that behave more or less as a cloud or electron gas. The Drude model was improved in 1933 by Arnold Sommerfeld and Hans Bethe, leading to the Drude-Sommerfeld-Model that takes into account quantum effects. In particular, in 1927 Somerfield and Bethe applied a branch of quantum physics known as statistical mechanics, or Fermi-Dirac statistics developed by Enrico Fermi and Paul Dirac. This is a particular case of particle statistics that determines the distribution of large numbers of electrons in the various energy levels that are available in atoms. Again, electron-electron interactions do not have to be considered, except for the Pauli Exclusion Principle, which states that no two electrons can occupy the same quantum state at the same time. Two electrons can occupy the same atomic or molecular orbital if they have opposite spin, a concept that arises in quantum mechanics. The significance for free radicals is that free radicals are defined as having one or more atomic or molecular orbitals with an unpaired electron.

These considerations lead to a more detailed physical explanation of how free electrons may be conducted in the surface layers of the earth and in the tissues of the human body, as well as how these electrons interact with free radicals in living tissues. Physical descriptions provide the most reliable and accurate picture relevant to this situation. The reason for this is that the chemical perspective focuses on atoms and molecules interacting with one another, dominated by atom-atom, atom-molecule or molecule-molecule collisions. The perspectives of physics, quantum physics, quantum chemistry and biophysics enable study of the forces and motions involved in chemical reactions at much smaller and more fundamental scales, the subatomic or electronic levels. Since free radicals are usually defined as molecules that have an unpaired electron, it is necessary to focus at the quantum electronic scale. As mentioned above, the very term, unpaired electron, relates to a phenomenon known as spin, a distinctly quantum phenomenon that is not referenced in classical physics.

Condensed matter physics recognizes that many of the concepts and techniques developed for studying fluid systems also apply to solids. For instance, the conduction electrons in an electrical conductor can form a type of "quantum fluid" with some properties that are similar to those of conventional fluids. Obviously, the existence of quantum fluids implies that the laws of quantum mechanics must be taken into consideration, expanding our understanding of what is usually referred to as electronic conduction.

In the past, it was thought that the term "quantum fluid" applied only to clusters of atoms or subatomic particles that condense under extreme conditions of pressure and temperature. Much research has been done to demonstrate the existence of unusual properties such as superconduction, superfluidity and quantum coherence that take place at low temperatures or with other extreme conditions.

Over the years it has been discovered that the extraordinary subatomic properties that were first demonstrated at low temperatures and other special conditions can also be exhibited at room temperature or at body temperature. Driving research in this field is the need to reduce the size and increase the efficiency of electronic technologies. Engineers are constantly looking for applications that take advantages of the extraordinary quantum properties of materials so they can develop efficient circuits composed of atoms or molecules.

There are two general types of condensation. A fermionic condensate is a superfluid phase formed by fermionic particles (electrons, protons or neutrons) at low temperatures. The earliest recognized fermionic condensate described the state of electrons in a superconductor. A system of identical fermions is called a Fermi gas or a free electron gas. If the temperature is low enough, the Fermi gas becomes "degenerate," a state that provides a good model of the conduction electrons in a metal, even at room temperature. Hence physicists describe the electron clouds in metals and semiconductors in relation to Fermi gases. This will be important below in the discussion of the semiconductor nature of both the tissues in the human body and the earth's crust.

Quantum physics recognizes two types of particles in nature, fermions and bosons. Fermions have half-integerspin, or spin $\frac{1}{2}$, whereas bosons have integer spin. Here the term, spin, should not be conceptualized as an actual rotation about an axis, as spin is usually viewed in the macroscopic world. Instead, spin is a phenomenon that arises in quantum statistics and is a major distinction between bosons and fermions. Atoms and photons are composed of bosons and have integer spin, and therefore obey Bose-Einstein Statistics. This means that groups of bosons are capable of being organized into the same quantum state to produce coherence, as in a laser or maser. Assemblies of particles, such as atoms and molecules, can also behave as bosons or fermions. Depending on the number of electrons, protons and neutrons, an atom can have integer or half-integer total spin and, therefore, be a boson or fermion, respectively. Electrons are the best known fermions, have half-integer spin, and obey Fermi-Dirac statistics, whose consequence is the Pauli Exclusion Principle—no two fermions can occupy the same quantum mechanical state at the same time. The Pauli Exclusion Principle accounts for important features of free radicals and their reactions with electrons, to be discussed below.

Under appropriate conditions, fermions such as electrons and bosons such as atoms can be condensed into unusual states of matter known as the fermionic condensate or the Bose-Einstein condensate, respectively.

Recent research has blurred the distinction between the fermionic and Bose-Einstein condensates. For example, a fermionic condensate of bosonic atoms was created in 2004, and a number of research groups have shown that a Bose-Einstein condensate can fermionize, i.e. develop properties related to electrons. These include excitons, which are electron-hole pairs and anyons, which are particles with statistics intermediate between Fermi and Bose statistics in two-dimensional space.

One of the leading theorists in the field of superconduction, Herbert Fröhlich, demonstrated that the Bose-Einstein condensation can take place in living tissues at body temperatures and pressures because of the high degree of order or crystallinity in certain cellular and tissue components. Again, it had been thought that Bose-Einstein condensation could only take place at extremely low temperatures, as was demonstrated by Eric Cornell and Carl Wieman in 1995 at the University of Colorado at Boulder NIST-JILA lab, using a gas of rubidium atoms cooled to 170 nanokelvin (nK). Under such conditions, a large fraction of the atoms collapsed into the lowest quantum state, at which point quantum effects become apparent on a macroscopic scale (Cornell E A, Weiman, C E, 2001; *Bose-Einstein condensation in a dilute gas; the first 70 years and some recent experiments*; Nobel Lecture, December 8, From *Les Prix Nobel. The Nobel Prizes 2007*, Edited by Tore Frängsmyr, [Nobel Foundation], Stockholm, 2002).

In essence, Fröhlich concluded that giant dipolar molecules such as proteins, nucleic acids and lipids in cellular membranes, which can have enormous electrical fields of some $10^7$ V/m across them, should vibrate intensely and coherently at characteristic frequencies and create a physical situation analogous to a Bose-Einstein condensation at body temperature. These vibrations can build up into collective modes of both electromechanical oscillations (phonons, or sound waves) and electromagnetic radiations (photons) that extend over macroscopic distances within the organism and perhaps also outside the organism. These electromechanical oscillators are coupled together to form an extended Fröhlich system.

Fröhlich began his work on biological coherence with a theoretical calculation that predicted a phenomenon. Fröhlich oscillations have now been repeatedly confirmed by experiment. A number of authors have criticized Fröhlich's application of coherence and Bose-Einstein condensation in biology, but the objections have been dealt with in other works.

The discovery that quantum effects become apparent on a macroscopic scale at body temperature in biological systems is extremely important as it allows theory and research on the movement of free electrons in cloud- or gas-like form through the tissues of the body. The phenomenon has been described as follows: the crucial distinguishing feature of Bose-Einstein condensates is that the many parts that go to make up an ordered system not only behave as a whole, they become whole: their identities merge or overlap in such a way that they lose their individuality entirely. This concept was first articulated by Albert Szent-Györgyi at the Korányi Memorial Lecture given in Budapest on Mar. 21, 1941, when he described the semiconductor nature of proteins: "If a great number of atoms is arranged with regularity in close proximity, as for instance, in a crystal lattice, the terms of the single valency electrons may fuse into common bands. The electrons in this band cease to belong to one or two atoms only, and belong to the whole system." And, "A greater number of molecules may join to form such energy continua, along which energy, viz., excited electrons, may travel a certain distance." (Szent-Györgyi, A., 1941, *Towards a new biochemistry?*, Science 93:609; Szent-Györgyi, A., 1941, *The study of energy levels in biochemistry*, Nature 148(3745):157-159). The concept of semiconduction in proteins encountered much resistance, but has now been accepted and has become a foundation of the new field of molecular nanoelectronics.

Because of barriers to communication between scientists working in different disciplines, the biological and biomedical significance of the discoveries of Bose, Einstein, Szent-Györgyi, Fröhlich and others is not as well appreciated as it might be. In terms of biology, the significance is that much of the living organism is composed of highly ordered molecular arrays or crystalline-like materials (connective tissues, cell membranes, muscles, rods and cones, microtubules in cilia, and so on), all of which can be described as being coupled oscillators and all of which will support the ordered conduction of electron clouds or gasses as described by Fröhlich and others.

The surface of the earth is likewise composed of materials that conduct electricity. The earth's surface is dominated by the oceans which are composed of water and dissolved minerals which render the oceans highly conductive. The solid crust can be classified either as 'continental' or 'oceanic'. Continental crust is on average older, more silica-rich and thicker than oceanic crust, but is also more variable in composition. Oceanic crust underlies most of the two-thirds of the Earth's surface. It has a remarkably uniform composition (mostly 49%±2% $SiO_2$) and thickness (mostly 7±1 km). The continental crust is composed mainly of basalt and granite. Basalt is a common gray to black volcanic or igneous rock. Volcanic rocks are usually fine-grained or aphanitic to glassy in texture. Aphantic (from the Greek αφανηζ, invisible) refers to certain typically dark-colored igneous rocks which are so fine-grained that their component mineral crystals are not detected by the unaided eye. They often contain clasts or fragments of other rocks and phenocrysts. A phenocryst is a relatively large and usually conspicuous crystal distinctly larger than the grains of the rock matrix. The word granite comes from the Latin granum, a grain, in reference to the coarse-grained structure of such a crystalline rock.

The dominant mineral in the earth's crust, $SiO_2$, (quartz), is a crystalline semiconductor and therefore capable of sustaining the movement of electrons much like the semiconductor materials that characterize the living state.

Not surprisingly, the conduction of electricity in the surface layers of the earth is well established (See Lanzerotti L J, and Gregon G P, 1986, *Telluric Currents: The Natural Environment and Interactions with Man-Made Systems*; Chapter 16 in Studies in Geophysics. The Earth's Electrical Environment, Geophysics Study Committee, Geophysics Research Forum, Commission on Physical Sciences, Mathematics, and Resources, National Research Council. Published by the National Academies Press, Washington D.C.).

Theory and measurement therefore show that free electrons migrate through the conductive surface layers of the earth as well as through the conductive tissues of the human body, provided the two systems, earth and body, are in conductive contact with each other.

Oxidation and reduction and reduction potential are frequently used but confusing terms in free-radical chemistry. There are serious limitations to the use of oxidation/reduction concepts when looking at free electron interactions with free radicals in the human body. First, the chemical species in living systems are not isolated as they are when their reduction potentials are measured in a standardized system. Reaction conditions make a big difference. Moreover, the standardized reduction potentials are always measured at 25° C. and corrected to pH=7.0, but the actual pH and temperature in living tissues can be quite different from these values. The Nernst equation can be used to correct for the values of concentration and temperature. The resulting "effective" reduction potential can be used to predict which reactions are feasible, but this does not mean that those reactions will actually occur under the conditions present in a particular tissue (for a discussion of oxidation-reduction potentials as applied to free-radical chemistry, and the limitations of this approach, see Halliwell B, and Gutteridge J M C, 1999, *Free*

Radicals in Biology and Medicine; Chapter 2, The chemistry of free radicals and related "reactive species." Oxford University Press, Oxford, UK, p. 36-104). Moreover, free radical reactions can be exceedingly fast, making it difficult to follow reaction rates based on changes in the concentrations of reactants and products.

A modern method for the direct study of free radical reactions is femtosecond spectroscopy, which makes it possible to observe what actually happens to a reacting molecule as it passes through its so-called transition state during which bonds are broken and formed. The transition state is as fast as the electrons and atoms in the molecule move—about 1000 m/second—about as fast as a rifle bullet. The times involved typically tens of femtoseconds (1 fs=$10^{-15}$ seconds). Ahmed Zewail developed a method for observing the transition state, giving birth to a new scientific field called femtochemistry. What is essentially the fastest camera in the world is used to film the molecules during a reaction and get a sharp picture of the transition states. The "camera" is a pulsed laser. The reaction is initiated by a strong laser flash and is then studied by a series of subsequent flashes to follow the events. The result is a slow motion image of how bonds are stretched and broken. Ahmed Zewail was awarded the Nobel Prize for showing the decisive moments in the life of a molecule—the breaking and formation of chemical bonds (Zewail A, 1999, *Nobel Lecture: Femtochemistry: Atomic-Scale Dynamics of the Chemical Bond Using Ultrafast Lasers*; From *Nobel Lectures, Chemistry* 7996-2000, Editor Ingmar Grenthe, World Scientific Publishing Co., Singapore, 2003).

Thus, there are complementary ways of looking at the phenomena described in this patent. What emerges from current experimentation and theory in the fields of condensed matter physics and quantum mechanics is a holistic perspective that places the free radical molecule in the inflamed tissue of a person who is in conductive contact with the earth at the end of a continuum encompassing the sun, the atmosphere, the earth's oceans and crust and the tissues of the body. Indications are that this physical arrangement allows the human body to be permeated with a cloud or gas or quantum fluid composed of electrons that are capable of neutralizing free radicals and thereby preventing or reducing inflammation and its pathological consequences. The electrons are separated enough so that they do not interact with each other, and they are relatively disconnected from the atomic cores of the matrix in which they move. The electrons do not really travel, as in a wire. They are better described as waves than as particles. They are in a quantum state such that they can form the electron pairs that complete the occupancy of atomic or molecular orbitals that would otherwise maintain the free radical in its highly reactive and potentially harmful state.

It is well established that negative charges (free electrons) are instantly attracted to positive charges (free radicals). (Coulomb's law: The electric force acting on a point charge as a result of the presence of a second point charge ((one positive and one negative)) attract one to the other). (Chemists use the term "electrophile" ((literally electron-lover)) to describe a reagent that attracts electrons. Most electrophiles are positively charged). Connecting the body to the earth automatically enables the conductive tissues of the body to become charged with earth's free electrons. When the body is charged with earth's mobile free electrons, excess or residual immune response free radicals have a readily available source of free electrons to couple with and reduce their oxidative state. This eliminates the need for residual immune system produced free radicals to oxidize healthy tissue to obtain their missing electrons. By readily reducing free radicals with earth's free electrons, oxidation of healthy tissue is naturally inhibited, which helps the immune response ROS free radicals to wind down properly.

To verify the effects of speeding recovery from acute trauma and preventing or reducing chronic inflammation in the body with application of earth's free electrons to the body, several research studies and a host of clinical case studies were performed. A series of clinical case studies (Amalu, supra) well document the therapeutic effectiveness of speeding recovery from acute trauma and preventing or reducing chronic inflammation and related health disorders by conductively coupling the body with the earth. The rapid healing of acute injuries and prevention or reduction of chronic inflammation that is consistently evidenced in the case studies support the concept that nature, throughout evolutionary time, relied upon earth's mobile free electrons as a primal source of antioxidants to prevent oxidation of healthy tissue. Further, in considering that the immune system's oxidative response mechanisms developed when humans and animals lived in conductive contact with the earth, the clinical case studies (Amalu, supra) strongly support that the modern practice of wearing synthetic soled shoes and living in environments that insulate the body from the earth is the primary contributor to the current epidemic of chronic inflammation and related health disorders (autoimmune diseases).

Current biomedical research (referenced above) confirms that chronic inflammation and autoimmune diseases are virtually epidemic in modern times. They include: high blood pressure, cardiovascular/heart disease, diabetes, multiple sclerosis and other neuromuscular diseases, respiratory disorders, digestive disorders, liver, gall bladder and kidney dysfunction, diseases of the colon, arthritis, chronic fatigue, osteoporosis, hormone imbalances, thyroid dysfunction, Alzheimer's, premature senility/dementia, as well as the continuing rise in cancer.

When the human body is conductively coupled with the earth by means of the present invention, the body naturally conducts and becomes charged with earth's mobile free electrons, i.e. it equalizes with and maintains the natural electrical potential of the earth. In this state earth's mobile free electrons are available throughout the body to readily reduce excess free radicals and thereby prevent oxidation of healthy tissue. Current biomedical research (referenced above) confirms that free radical oxidation of healthy tissue is the underlying cause of chronic inflammation and autoimmune disease. Clinical case studies (Amalu, supra) show that restoring the earth's natural surface charge of free electrons to the body consistently speeds recovery from acute trauma and prevents or reduces chronic inflammation.

Accordingly, there is a need for a method to conduct and apply the earth's mobile surface charge of free electrons to the bodies of humans and animals to treat acute injuries or to help reduce and prevent chronic inflammation and to treat inflammation-related autoimmune diseases. Such methods should be capable of being used while sleeping, during prolonged periods of sitting, standing and during other activities when the body is residing in an environment that would otherwise insulate the body from conductive contact with the earth. The present invention fulfills this need.

SUMMARY OF THE INVENTION

The present invention resides in a method for reducing and preventing inflammation and treatment of inflammation related autoimmune diseases. More particularly, the present invention relates to a method of speeding recovery from acute injury and inhibiting or preventing the expression of chronic inflammation in an animal or human by conductively coupling the body with the earth to conduct earth's mobile surface charge of free electrons from the earth to the body to restore the bodies natural supply of free electrons to help reduce and prevent residual immune response reactive oxygen species (ROS) free radicals from oxidizing normal tissue. When an animal or human body is naturally charged with earth's free electrons, residual immune response ROS free radicals have a readily available source of free electrons to rapidly reduce their oxidative state. This helps to inhibit ROS free radical oxidation of healthy tissue and thereby speeds recovery from acute injury and prevents or inhibits the promotion and manifestation of chronic inflammation and inflammation-related health disorders in the body.

Sufficient conductive contact between the body and the surface of the earth, and its beneficial consequences, can be achieved most naturally and preferentially through the bare feet. This contact is preferably established via direct contact between the feet and a conductive footpad or bed sheet. Conductivity is preferably established with fabrics containing silver fibers. Silver provides improved conductive coupling with the feet and also gives the invention advantageous anti-microbial, anti-bacterial and anti-fungal properties.

The present invention resides in a process for reducing tissue inflammation in a living body, comprising the steps of providing a grounded plane, bringing the body into extended contact with the grounded plane, and reducing the oxidative state of residual immune response free radicals in the body using free electrons provided through contact with the grounded plane. The grounded plane may comprise a conductive pad conductively coupled to a grounded anchor placed in the earth. The step of bringing the body into contact with the grounded plane comprises conductively coupling the body with the conductive pad.

The step of reducing the oxidative state includes the step of conducting a mobile surface charge of free electrons from the earth to the body. The step of conducting a mobile surface charge includes the step of restoring the body's natural supply of free electrons and reducing residual immune response reactive oxygen species free radicals in the body.

The reducing step includes the step of speeding recovery of the body from acute injury. The reducing step also includes the step of inhibiting expression of chronic inflammation in the body. The reducing step also includes the step of inhibiting free radical oxidation of healthy tissue in the body. The bringing step includes the step of bringing the grounded plane into contact with a body's bare feet.

Thus, there are several objectives of the present invention, including reducing or preventing inflammation in an animal or man by supplying or applying the mobile negative surface charge of the earth to the body to provide an abundant supply of free electrons to the body to reduce excess free radicals in the body produced during a normal immune response, thereby speeding recovery and preventing or inhibiting the possible oxidation of healthy tissue, which comprises a conductive pathway between the earth and the body sufficient to maintain a natural flow of free electrons from the earth to the body, as would occur in nature if said animal or man were standing barefoot on the earth.

It is another object of the present invention to conduct and maintain the earth's mobile negative surface charge of free electrons on the body to supply the body with an abundant supply of free electrons to reduce or prevent inflammation via a conductive pathway consisting of connecting a conductive floor covering that is conductively connected to a dedicated ground wire that is connected to a ground anchor placed in the earth or connected to the electrical ground or common ground wire of a modern home or workplace electrical system in which an animal or man maintains barefoot contact with the conductive flooring or the animal or human wears conductive footwear to maintain conductive contact between the body and the earthed conductive floor covering.

It is another object of the present invention to conduct and maintain the earth's mobile negative surface charge of free electrons on the body to supply the body with an abundant supply of free electrons to speed recovery from acute injury and reduce or prevent chronic inflammation via a conductive pathway consisting of a mattress or sleeping pad that is covered with fabric containing conductive fibers that is conductively connected to a dedicated ground wire that is connected to a ground anchor placed in the earth or connected to the electrical ground or common ground wire of a modern home or workplace electrical system in which an animal or human maintains barefoot or body contact with the conductive mattress via sleeping on sheets that contain conductive fibers that make contact between the body and the conductive mattress covering.

It is another object of the present invention to conduct and maintain the earth's mobile negative surface charge of free electrons on the body to supply the body with an abundant supply of free electrons to speed recovery from acute injury and reduce or prevent inflammation via a conductive pathway consisting of a fabric tape or body band containing conductive fibers that are conductively connected to a dedicated ground wire that is connected to a ground anchor placed in the earth or connected to the electrical ground or common ground wire of a modern home or workplace electrical system in which an animal or human maintains skin contact with the conductive fibers of the fabric tape or body band.

It is another object of the present invention to conduct and maintain the earth's mobile negative surface charge of free electrons on the body to supply the body with an abundant supply of free electrons to speed recovery from acute injury and reduce or prevent inflammation via a conductive pathway consisting of an electrode patch that is conductively connected to a dedicated ground wire that is connected to a ground anchor placed in the earth or connected to the electrical ground of a modern home or workplace electrical system in which an animal or human maintains skin contact in an area of the body with acute injury or localized inflammation.

It is another object of the present invention to conduct and maintain the earth's mobile negative surface charge of free electrons on the body to supply the body with an abundant supply of free electrons to reduce or prevent inflammation via a conductive pathway consisting of a chair or seating mechanism that is covered with fabric containing conductive fibers that is conductively connected to a dedicated ground wire that is connected to a ground anchor placed in the earth or connected to the electrical ground or common wire of a modern home or workplace electrical system in which an animal or human maintains conductive contact with the earthed seat covering fabric with either bare skin contact or wearing clothes containing conductive fibers that make contact with conductive fiber in chair or seat covering conductive fabrics or via conductive hydration of clothing from normal body perspiration that occurs when sitting.

It is another object of the present invention to conduct and maintain the earth's mobile negative surface charge of free electrons on a human body to supply the body with an abundant supply of free electrons to reduce or prevent inflammation via a conductive pathway consisting of clothes made from fabrics that contain conductive fibers that are conductively connected to a dedicated ground wire that is connected to a ground anchor placed in the earth or connected to the electrical ground or common wire of a modern home or workplace electrical system.

It is yet another object of the present invention to use a connecting device containing a circuit testing apparatus to test the working order of an electrical circuit outlet ground or common ground port for conducting earth's mobile negative charge to an animal or human grounding apparatus. The connecting device displays a green light if the outlet is correctly wired and a working electrical ground wire is connected to the outlet ground port. This device may be fitted with one or more earthing port receptacles for connection of more than one animal or human earthing apparatus. Further each port will contain a current limiting device to protect against harm from an electrical event.

It is another object of the present invention to conduct and maintain the earth's mobile charge of free electrons on a human body to supply the body with an abundant supply of free electrons to reduce or prevent inflammation via a conductive pathway consisting of a conductive desk pad or computer mouse pad or wrist pad made with a conductive surface layer that is conductively connected to a dedicated ground wire that is connected to a ground anchor placed in the earth or connected to the electrical ground of a modern home or workplace electrical system.

Other features and advantages of the present invention will become apparent from the following more detailed descriptions, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE INVENTION

The present invention resides in a method to treat acute injury or to reduce and prevent inflammation and to treat chronic inflammation-related autoimmune disorders. More particularly, the present invention relates to a method of treating acute injuries and/or inhibiting the expression of chronic inflammation in an animal or human by conductively coupling the body with the earth to conduct earth's mobile surface charge of free electrons from the earth to the body in order to restore the body's natural supply of free electrons and thereby reduce and prevent residual immune system produced reactive oxygen specie free radicals from oxidizing normal tissue. When an animal or human body is naturally charged with earth's mobile free electrons, residual immune system produced free radicals have a readily available source of free electrons to rapidly reduce their oxidative state. This inhibits free radical oxidation of healthy tissue and thereby speeds recovery from acute injury and prevents or inhibits the promotion and manifestation of chronic inflammation and inflammation-related health disorders.

U.S. Pat. No. 6,683,779 discloses a personal grounding system for collecting and removing unnatural electrical charges from a human body. The grounding pad comprises between 10% and 20% carbon fibers. The grounded anchor is placed directly into the earth. The grounding pad could also comprise a sitting pad positionable on a vehicle seat, and wherein the grounding anchor comprises a metal component of a vehicle. Disclosure of this United States patent application is hereby incorporated by reference into this specification. The purpose of the present patent is to disclose discoveries obtained during the application of the '779 patent, and to further disclose improvements and enhancements to the methods of the previous patent based on further research and observation.

Experience with use of the previous patent has revealed that re-establishing electrical contact of a human or animal body with the earth produces rapid and extremely valuable anti-inflammatory effects, which therefore favor its application in the treatment of numerous inflammatory conditions.

This disclosure provides advantages and enhancements over the '779 patent, that disclosed grounding comprising a sitting or sleeping pad and including a mesh layer substrate comprised of a plurality of electrically conductive carbon fibers, and a conductor substantially extending across the substrate in conductive contact with the fibers, the grounding pad being configured to make field or conductive contact with the human body; a ground lead having a first end conductively coupled to the grounding pad conductor; and a grounded anchor conductively coupled to a second end of the ground lead. The '779 patent also provided for body bands, conductive patches and a conductive seat for use in a vehicle.

The chair and sleeping pads described in the '779 patent are effective, but it has been discovered that in order for the grounding pad to be in direct conductive contact with the skin of a human body through a covering sheet (in the case of a sleeping pad) or through clothing (in the case of a chair or sitting pad) it is essential for said body to produce perspiration, and thereby moisten or hydrate the sheet or clothing, respectively, to render them conductive. This slows and in many cases prevents the natural migration of electrons from the earth to the body.

The previous invention also allowed for conductive coupling with the body through an adhesive electrode patch or through body bands containing conductive fabrics that could be placed around an ankle, foot or wrist, for example. While these methods are effective, they require a cord be attached to them while being used. This was found to be inconvenient for most users; whereas a conductive footpad or bed pad requiring only barefoot contact is more convenient for use in most living space and work place environments.

The method of the invention comprises administration to an animal or human the natural negative surface charge of free electrons of the earth in an amount similar to the amount that would occur in nature if said animal or human were standing barefoot on the earth. The requirement of maintaining earth's negative surface charge of free electrons on the body to therapeutically speed recovery from acute injury and/or reduce inflammation is shown to vary from minutes to hours to weeks depending upon the amount and extent of inflammation and inflammation related disease in the body. To prevent inflammation it is recommended that the body maintain conductive contact with the earth for a routine amount of time on a daily basis.

The method of the present invention grounds the body, such as by using the devices and systems in the '779 patent. More preferably, a grounding pad or strip is either directly attached to the body, or is conductively coupled to the body, the grounding pad or strip being connected to a ground anchor placed directly in the earth. Such grounding pads or strips include a mesh layer substrate comprised of a plurality of silver fibers, such as silver coated nylon fibers, having a silver content typically comprising 5% of the fabric. Typically, this substrate comprises 95% polyester, nylon or cotton and 5% silver-suffused monofilament nylon knitted into a conductive grid pattern. Although 5% silver fiber content is preferred, the grounding pad or strip silver fiber content may vary, such as between 1% and 10% silver fibers.

The grounding pad or strip can take various forms, such as a pad placed directly beneath the feet of the individual, a strip or pad removably attached to an appendage of the body, the pad may be in the form of a large rug or flooring surface, the mesh fabric as described above may be used to line a chair or sleeping bag or a bed sheet. The important aspect of the present invention is that there is conductive contact between the body and the grounding pad such that electrons can freely flow therebetween.

The grounding pad or strip is conductively coupled to the ground anchor by means of a ground lead extending from the pad or strip to either the ground anchor directly, or more typically to a wall plate connected to the electrical ground of the building or home. For example, the ground lead may be directly connected to the ground lead or other suitable wiring of the home or building. This may be done, for example, utilizing a banana clip or other appropriate conductive connector.

In a particularly preferred embodiment of the invention, a safety interface device is plugged into an electrical outlet of the home or building which includes a fuse or current limiting resistor to prevent potential harm from an electrical event. This device may also be provided with an electronic circuit and indicators that show that the apparatus is functioning properly, and that there is a free flow of electrons through the apparatus from the ground to the ground lead and pad or strip.

As described in the '779 patent, one end of the ground lead can include a connector such as a banana clip which can be removably attached to a wall plate. Although the connector can comprise a plug, such as a banana clip, for insertion into an outlet-like aperture of a wall plate, the connector may also comprise a snap-fit connector of the circular or ring variety which can be snapped onto a mating member of the wall plate so that children cannot accidentally insert the connector into an electrical socket. Alternatively or additionally a snap-fit connector of the circular or ring variety can be snapped onto a mating member coupled to the grounding pad.

Figure 1:
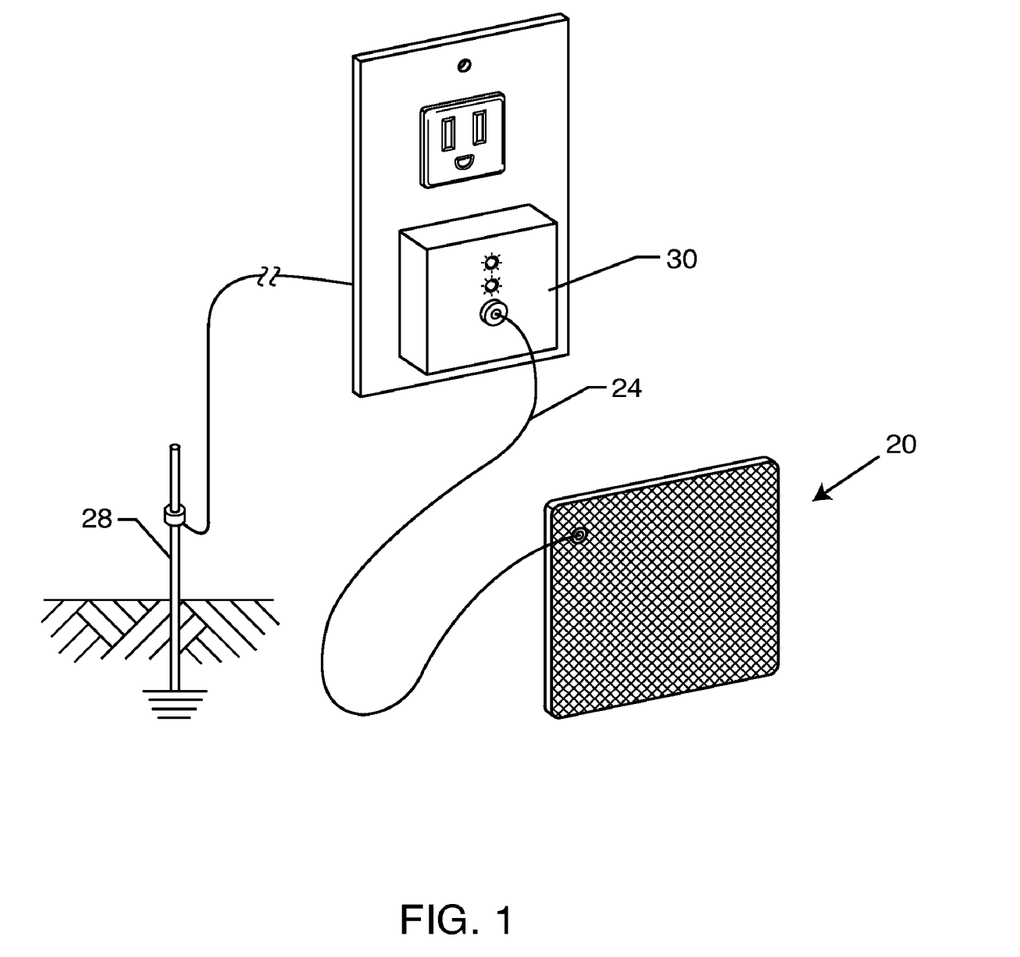
FIG. 1 is a diagrammatic view of an exemplary grounding system used in accordance with the present invention, including a grounding pad, grounding lead, interface device, and a grounding anchor placed directly in the earth.

A meter or fuse or current limiting resistor may be associated with the system, and typically installed within the ground lead 24 or electrical outlet ground port 30, as illustrated in FIG. 1. The fuse or current limiting resistor is intended to prevent potential harm from an electrical event.

A ground system interface device 30 comprising a box containing electrical contact terminals that are connected to a test circuit residing in the device 30 that test the wiring configuration of the outlet and confirms that an earth ground wire is connected to the third prong electrical outlet port. If the outlet wiring is correct and a ground connection exists a green light will indicate that the interface device is in working order. This device will also contain banana jack type ground ports for connecting ground leads from personal grounding devices to the earth ground system as illustrated. Each ground port outlet of the device will contain an inline current limiting resistor, such as a 1 megohm resistor, which meets current known or established standards to protect a grounded person against harm from an electrical event. Further, a mechanism to reduce electrical noise on the common ground wire may be embedded inline on the ground port side within the test interface device to allow use of the common ground wire in homes that do not have a standard third wire electrical ground system.

The systems described above have been used in experiments with test patients having various physical maladies, including inflammation and inflammation-related chronic diseases. The earthing or grounding systems used in the studies consisted of either a conductive sleep pad or two EKG-type adhesive electrode patches, one placed on the bottom of each foot. A 50-foot ground cord or lead with a snap attachment on one end (attached to the electrode patches or the conductive sleep pad), with another end attached to a 12-inch earthing rod placed in the earth (soil) outdoors. The purpose of using these devices and systems for the studies was to replicate a person standing barefoot or sleeping directly on the earth while residing or being located in an environment that insulates the body from the earth to measure the physiological effects that occur from conductively reconnecting the body with the earth.

The first study of the advantages of the '779 patent involved 60 people with sleeping difficulties and chronic muscle or joint pain. (See, Ober, A. Clinton, *Grounding the human body to neutralize bio-electrical stress from static electricity and EMFs*; ESD Journal, the ESD and Electrostatics Magazine, 2001). Sleeping on a grounded mattress pad for 4 weeks led to significant improvements in sleep, muscle relaxation, and reduction of chronic back and joint pain. Specifically, 85% of the subjects went to sleep quicker, 93% reported sleeping better throughout the night, 100% reported feeling more rested in the morning, 82% experienced reduction in muscle stiffness, 74% experienced less chronic back or joint pain, and 78% reported improved general health. Close examination of the results of certain subjects in this study led to the question why some subjects sleeping in very low EMF exposure environments vs. subjects sleeping in very high EMF exposure environments reported similar reductions in chronic pain. It was this observation that led to further investigations and eventually to the discovery that being conductively connected to the earth alone produced the reductions of inflammation related chronic pain.

A second study by M. Ghaly, MD and D. Teplitz of the advantages of the '779 patent showed that use of the grounded mattress pad over an 8-week period normalizes the day/night hormone cortisol secretion rhythm. It is well known that cortisol is a primary inflammation marker. The following is an overview of the study: Diurnal cortisol secretion levels were measured and circadian cortisol profiles were evaluated in a pilot study conducted to test the hypothesis that grounding the human body to earth* during sleep will result in quantifiable changes in cortisol. It was also hypothesized that grounding the human body would result in changes in sleep, pain, and stress (anxiety, depression, irritability), as measured by subjective reporting. Twelve (12) subjects with complaints of sleep dysfunction, pain, and stress were grounded to earth during sleep for 8 weeks in their own beds using a conductive mattress pad. Saliva tests were administered to establish pre-grounding baseline cortisol levels. Levels were obtained at 4-hour intervals for a 24-hour period to determine the circadian cortisol profile. Cortisol testing was repeated in the same manner at week 6. Subjective symptoms of sleep dysfunction, pain, and stress were reported daily throughout the 8-week test period. Measurable improvements in diurnal cortisol profiles were observed, with cortisol levels significantly reduced during night-time sleep. Subjects' 24-hour circadian cortisol profiles showed a trend toward normalization. Subjectively reported symptoms, including sleep dysfunction, pain, and stress, were reduced or eliminated in nearly all subjects. The results indicate that grounding the human body to earth ("earthing") during sleep reduces night-time levels of cortisol and resynchronizes cortisol hormone secretion more in alignment with the natural 24-hour circadian rhythm profile. Changes were most apparent in females. Furthermore, subjective reporting indicates that grounding the human body to earth during sleep improves sleep and reduces pain and stress. Ghaly M, MD, and Teplitz D, MA; *The Biological Effects of Grounding the Human Body During Sleep, as Measured by Cortisol Levels and Subjective Reporting of Sleep, Pain and Stress*, Journal of Alternative and Complementary Medicine, November, 2004, Volume 10, Number 5, pages 767-776.)

The following subjective case study reports from the Gahly, Teplitz study show that all participants were experiencing pre-study symptoms from known inflammation related health disorders. All but one subject reported significant reductions of these symptoms at the end of the study. The results in total provide significant evidence that conductively coupling the body to the earth consistently reduces chronic inflammation and promotes recovery from a wide range of inflammation-related health disorders.

Subject 101 (female age 24)—Menstrual cycle regular
Pre-Study Complaints
Long time to fall asleep, wake up after several hours and can't sleep again; wake up exhausted
Daily headaches
Migraine one week before periods for last 4 years
Hip misaligned since labor with child 2 years ago
PMS: cramps, mood swings, bloating, irritability, depression, weight gain, easily upset, hot flashes
Digestion: bloating, nausea, diarrhea, gas, constipation
End of Study Reports
"Decreased time to go to sleep"
"Able to fall back asleep after waking-up"
"Wake up refreshed instead of exhausted"
"No more daily headaches"
"Re: PMS—decreased food cravings, decreased bloating, depression and hot flashes"
"No more nightmares"
"Digestion improved with less bloating, constipation and nausea"
Additional End of Study Comments
"By the third night [on the mattress pad] I slept through the night and it did not take me as long to go to sleep. I've had trouble sleeping for 17 years and was constantly waking up through the night . . . and now if I do wake up in the middle of the night it is because my son has woken me and even after that it only takes me a few minutes to go back to sleep. In the morning I feel extremely refreshed and ready to start my day . . . I wouldn't want to give my mattress pad up for anything."
Subject 102 (female age 53)—Post Menopausal
Pre-Study Complaints
Difficulty going to sleep
Wake up 2-3 times a night for last 3 years
Whiplash (cervical sprain 24 years ago, re-injured 2 months ago)
Muscle cramps in legs
Chronic muscle pain through-out body (myofacial)
Hot flashes
End of Study Reports
"Fall asleep faster and easier"
"My neck pain is lessened"
"My leg and foot cramps have lessened"
"Helped my chronic pain be greatly reduced"
"Arm and lower back pain gone"
"TMJ problem significantly improved"
"Reduction in hot flashes"
Additional End of Study Comments
"Before using the mattress pad, I had a chronic pain in my left upper arm and lower back which were both totally gone the very first week and have not returned."

Subject 103 (female age 50)—Menstrual cycle regular
Pre-Study Complaints
Trouble falling asleep since childhood
Trouble waking up from deep sleep
Fatigued
Muscle aches and leg cramps—many years
Lower back pain and intestinal pressure due to uterine fibroids
PMS: fibrocystic breast tenderness, bloating, cramps, irritability, mood swings, easily upset, food cravings
Night sweats
TMJ causing occasional headaches
End of Study Reports
"Less stress about going to sleep after a lifetime's worth of sleep disorders"
"Somewhat less trouble falling asleep"
"Have gradually woken up feeling more refreshed in the morning whereas I almost always felt fatigued upon arising"
"Don't need coffee in the morning to get going"
"Leg cramps almost completely gone"
"Less backache and pain"
"Less PMS and even less fibrocystic"; "Less cramps and irritability with PMS"
"More even tempered"
"TMJ greatly reduced"
Additional End of Study Comments
"I've definitely had a greater sense of well-being and feel a subtle sense of lightness and ease. A low-grade, background feeling of stress that I've always had seems to be diminished."
Subject 104 (female age 42)—Menstrual cycle regular
Pre-Study Complaints
Trouble falling asleep
Waking feeling tired; Trouble waking up from nap
Light, restless sleep.
Fibromyalgia since 1992 car accident; a lot of joint pain—arms, legs, ankles
Gastrointestinal upset—gas
End of Study Reports
"The general quality of my sleep improved—not immediate, but a gradual change"
"Sleeping much deeper"
"A lot less fatigue because of less pain"
"My fibromyalgia has improved considerably because of diminished pain and fatigue"; "The joint pain is gone with occasional pain in the left arm"
"I am feeling much better, I haven't been sick at all."
Additional End of Study Comments
"I think the mattress pad is extremely beneficial and I hesitate to sleep on anything else."
Subject 106 (female age 51)—Post Menopausal (last period one year ago)
Pre-Study Complaints
Some trouble falling asleep
Wake up from hip pain; also wake up from a hot flash between 4 and 5 AM
Wake up with a headaches every morning (last 3 months)
Wake up feeling groggy (last 3 months)
Wake up tired
Hot flashes all day (for one year) as well as during sleep
Hip pain, possible arthritis (1-2 years)
End of Study Reports
"Disappointed that I did not sleep any better and my joint aches are worse than when I started"
"Less occurrence of hot flashes"
Additional End of Study Comments "No significant change except for decrease in daytime hot flashes."

Subject 107 (female 52)—Post Menopausal

Pre-Study Complaints

Sleep very lightly

Wake up feeling tense several times during the night

Wake up feeling tired in morning

Feel tired during day

Pain in left hip, sporadic for several years (began few years ago)

Allergies (food and airborne) since age 13

Digestion: gas

End of Study Reports

"Have felt more rested and feel like I need an hour less sleep per night"

"Deeper relaxation"

"Stopped having any pain at all in my left hip"

"First few days, I experienced tingling and heat in areas of my previous physical injuries—similar to an acupuncture treatment. After approx. 3 days, the feelings subsided, and the vague sense of having a previous injury has subsided."

"Allergies have definitely lessened"

"Better digestion"

"I noticed that I stopped clenching my jaw at night"

Additional End of Study Comments

"It's getting back into the rhythm of the earth."

"My husband, not part of this study, began sleeping fewer hours, has more energy, and has stopped snoring."

Subject 108 (female age 44)—Menstrual cycle regular, periods heavy

Pre-Study Complaints

Trouble sleeping (not as heavy as before)

Wake up 2-3 times each night with physical discomfort

Anemic one year

Less energy than in past

Numb fingers left hand 4 months, carpal tunnel

PMS: bad cramps, painful heavy periods and uterine fibroids many years, breast tenderness, mood swings, weight gain Hot flashes at night [or may be night sweats]

End of Study Reports

"Gradually sleeping better"

"Two episodes of waking up between 4:30 and 5:30 with anxiety that is intense upon awakening, then subsides to lower level but remains during the AM, gradually subsiding by noon or 1:00 PM. First episode was 5 days at the beginning of study and second episode was 8 days at the end of the study" [subject has past history of anxiety attacks; subject reports stress in daily life due to problems in relationship]

"Less numbness in hand and fingers, especially at night; not needing to wearing a brace at night"

"Menstrual period not as severe; cramps not as strong"

"Feeling better physically and emotionally"

Additional End of Study Comments

"My experience has been strange. I don't know what to think"

Subject 109 (female age 31)—Irregular menstrual cycle; period ceased for one year and restarted 3 weeks prior to study start date, then ceased again during study Pre-Study Complaints Problems getting to sleep Trouble sleeping, discomfort from neck, toss and turn till 3 AM Feel unrested in the morning PMS: bloating, breast tenderness, weight gain, acne (during menstrual periods)

Allergic to some foods (last 2 years)

Digestive problems: gas, constipation, bloating, heartburn

End of Study Reports

"At first my body responded quickly by feeling completely relaxed. After a week I went through several weeks of soreness in my neck area due to an increase in stress [subject reported crisis at work along with stress from planning her wedding]. I couldn't get comfortable—woke up feeling unrested. But even though I've been dealing with these stress-related struggles, I've noticed I sleep a lot more comfortably overall than 1 have in the past couple of years."

"Deeper relaxation once I get to sleep"

"Digestive system is getting better . . . less stomach pain and bloating"

Additional End of Study Comments

"My overall experience has been very positive"

Subject 110 (male age 72)

Pre-Study Complaints

Trouble falling asleep

Wakes up during the night

Don't want to wake up in morning

No pain

Some depression since surgery (aortic aneurysm ruptured 2½ years ago)

Digestion: gas, diarrhea

End of Study Reports

"Falling to sleep more quickly"

"Falling to sleep more quickly after going to the bathroom at night"

"Sleep is deeper"

"Dreams more vivid"

"Feeling somewhat more refreshed upon awakening"

"Stress and tension is improving"

"No more pain"

"Digestion is better"

Additional End of Study Comments

"The mattress pad is a very good health aid by helping you sleep deeper and relaxing you from stress and tension."

Subject 111 (male age 37)

Pre-Study Complaints

No problem going to sleep but sleep is not as deep as it should be

Wake up not feeling rested (4 years)

Sleep 7 hours at night. Need 2-3 hours more

Wake up feeling achy in back

Knee joint ligament problems—knee goes out of joint (several years)

Skin irritation/fever blisters

End of Study Reports

"My overall experience was impressive. I felt from the very first time a very relaxing effect. It is like you lay down and don't want to move"

"Definitely slept better"

"Woke up in a better physical and psychological state."

"Felt calmer and with better mood"

"Felt more centered and patient"

"Felt more relaxed"

Additional End of Study Comments

"I felt the physical effect of the pad, but I also felt the soothing psychological and spiritual effect of being connected to Mother Earth. It's like sleeping on your mother's lap again."

Subject 112 (male age 50)

Pre-Study Complaints

Sleep deeply 4 hours and then sleep is not restful
Get fatigued during the day (several years)
Arthritis (several years); achy joints
Leg cramps
Tore rotor cuff (one year ago)—almost better
Bone spur on left heel (started months ago)
Digestion: acid stomach problems, heartburn and gas
End of Study Reports
"Better sleep. I hardly wake up from early morning dreams where I used to wake up every night."
"I wake up more refreshed and my aching joints are almost gone."
"Less body pain in morning"
"Feeling better the rest of the day"
"My shoulder and heel have almost completely healed"
"Leg cramps are much less frequent"
"Stomach reflux has disappeared"
Additional End of Study Comments
"Something definitely worth trying if you are having problems with sleeping."
Subject 113 (male age 39)
Pre-Study Complaints
Trouble falling asleep
Wake up all through the night for a few minutes [subject reports his 4 dogs wake him up by barking frequently]. Trouble getting back to sleep
Sometimes wake up from shoulder and back pain
Tired in the day
Occasional headaches
Occasional sore muscles in shoulders and back from basketball or heavy lifting
Some back and hip pain
Digestion: gas and heartburn
End of Study Reports
"Fall asleep quicker"
"Seem to sleep deeper"
"No trouble falling back to sleep"
"In the morning I do not want to get out of bed"
"No shoulder pain"
"Less headaches"
"Digestion/heartburn less"
Additional End of Study Comments
"Sleep was better"

A third study conducted by G. Chevalier and colleagues measured changes in electrophysiological and physiological parameters from coupling the body with the earth. Fifty-eight healthy adult subjects (30 controls) participated in a double blind pilot study. Earthing was accomplished with a conductive adhesive patch placed on the sole of each foot. An earthing cord led outdoors to a rod driven into the earth. A biofeedback system recorded electrophysiological and physiological parameters. Upon earthing, all subjects presented an abrupt change in rms values of surface electromyograms (SEMGs) from right and left upper trapezius muscles. Signal variance in rms muscle potentials also increased significantly. The results of the Chevalier study show that conductively coupling the body to earth significantly affects the electrophysiological properties and the autonomic balance of the body. Chevalier G, PhD, Mori, Kazuhito, PhD, Oschman, James L., PhD, *The Effect of Earthing (grounding) on Human Physiology*, European Biology and Bioelectromagnetics, http://www.ebab.eu.com/dsp_abs.asp?s_aid=41&s_vol=1&s_iss=5.)

A fourth investigative study using the prior disclosed invention in testing the effectiveness in enhancing human performance, speeding injury repair and facilitating recovery has been performed by Jeffrey Spencer, D.C., who used the method to treat high profile athletes, including members of the US Professional Cycling Team. Spencer reported that the success of the Lance Armstrong team in their final three Tour de France victories (2003, 2004 and 2005) in part is due to the rapid healing and recovery produced by application of the prior invention. The following summarizes the clinical outcomes observed on the Tour.

1. Sleep was universally improved.
2. Tendonitis (inflammation) was virtually eliminated
3. Wound healing (abrasions) was vastly accelerated
4. All members of the team completed the Tour
5. Illness frequency and duration were much diminished over previous Tours.
6. Consistency of performance was significantly improved
7. Team morale remained high throughout the entire Tour
8. Recovery from exertions and injuries of the previous day was extremely high Minkoff, David I., M.D., *Best Cases in Biological Medicine*, Series #6, Explore! Volume 13, Number 6, 2004).

A fifth study was an electrical study using the prior disclosed invention to define the electrical network model of the human body and to measure and confirm the effects of applying earth ground to the body to measure reduction of environmentally induced body voltages. The study was performed by R. Applewhite. Voltage induced on a human body by capacitive coupling to the external environment was measured using a high-impedance measurement head. The body was then earth grounded by means of a Conductive Patch and a Conductive Bed Pad. Each method reduced the coupled 60 Hz mains voltage by a factor of at least 70. This result, along with the measurement of the voltage drop across an in-line resistance in the Conductive Patch provided evidence of a simplified electrical network model of the human body and the flow of electricity between the earth and the human body. (Applewhite, Roger, P. E., *The Effectiveness of a Conductive Patch and a Conductive Bed Pad in Reducing Induced Human Body Voltage Via the Application of Earth Ground*, 2004.)

A sixth study was performed by William Amalu, DC, DABCT, FIACT: (Amalu, supra). The case studies presented were performed at an out-patient clinical treatment center in Redwood City Calif. The subjects were randomly selected from the treatment database as they presented for care. Each subject consented to inclusion in the study. Pain levels were assessed and followed using the standardized fourpoint visual analogue pain scale. Thermal imaging of each subject was undertaken utilizing standardized pre-examination preparation protocols and strict image acquisition according to published guidelines. Some of the subjects were supplied with an earthing sleep system consisting of bedding, containing conductive fibers, which was placed on top of the subject's mattress and thereafter connected to the earth via a conductive ground cord and an earthed ground rod. Other subjects were given clinical earthing treatments, which entailed the use of conductive electrode adhesive patches that were attached to the skin at specific points and thereafter coupled to the earth via a conductive ground wire that was connected to an earthed ground rod. All of the subjects were followed over time and their results recorded and summarized. Use of high-resolution medical infrared imaging as an objective assessment of both inflammatory and neurophysiologic conditions demonstrated significant immediate changes in both acute and chronic inflammation-related conditions.

The research and case studies reveal that conductively connecting the body to earth effects the electrophysiology of the body and produces rapid resolution of both acute and chronic inflammation and its numerous consequences using the methods disclosed in the prior patent. The research to date confirms that re-establishing conductive contact of a human or animal body with the earth produces rapid and extremely valuable anti-inflammatory effects which favor its application in the treatment of numerous inflammatory conditions.

Although several embodiments of the invention have been described in detail for purposes of illustration, various modifications may be made without departing from the spirit and scope of the invention. Accordingly, the invention is not to be limited, except as by the appended claims.

What is claimed is:

1. A process for reducing tissue inflammation in a living body, comprising the steps of:
   providing a grounded plane;
   bringing the body into extended contact with the grounded plane; and
   reducing the oxidative state of residual immune response free radicals in the body using free electrons provided through contact with the grounded plane.

2. The process of claim 1, wherein the grounded plane comprises a conductive pad conductively coupled to a grounded anchor placed in the earth.

3. The process of claim 2, wherein the bringing step comprises conductively coupling the body with the conductive pad.

4. The process of claim 2, wherein the reducing step includes the step of conducting a mobile surface charge of free electrons from the earth to the body.

5. The process of claim 4, wherein the conducting step includes the step of restoring the body's natural supply of free electrons and reducing residual immune response reactive oxygen species free radicals in the body.

6. The process of claim 1, wherein the reducing step includes the step of speeding recovery of the body from acute injury.

7. The process of claim 1, wherein the reducing step includes the step of inhibiting expression of chronic inflammation in the body.

8. The process of claim 1, wherein the reducing step includes the step of inhibiting free radical oxidation of healthy tissue in the body.

9. The process of claim 1, wherein the bringing step includes the step of bringing the grounded plane into contact with a body's bare feet.

10. A process for reducing tissue inflammation in a living body, comprising the steps of:
    providing a grounded plane comprising a conductive pad conductively coupled to a grounded anchor placed in the earth;
    bringing the body's bare feet into extended contact with the grounded plane; and
    reducing the oxidative state of residual immune response free radicals in the body using free electrons provided through contact with the grounded plane.

11. The process of claim 10, wherein the bringing step comprises conductively coupling the body with the conductive pad.

12. The process of claim 10, wherein the reducing step includes the step of conducting a mobile surface charge of free electrons from the earth to the body.

13. The process of claim 12, wherein the conducting step includes the step of restoring the body's natural supply of free electrons and reducing residual immune response reactive oxygen species free radicals in the body.

14. The process of claim 10, wherein the reducing step includes the step of speeding recovery of the body from acute injury.

15. The process of claim 10, wherein the reducing step includes the step of inhibiting expression of chronic inflammation in the body.

16. The process of claim 10, wherein the reducing step includes the step of inhibiting free radical oxidation of healthy tissue in the body.

17. A process for reducing tissue inflammation in a living body, comprising the steps of:
    providing a grounded plane comprising a conductive pad conductively coupled to a grounded anchor placed in the earth;
    bringing the body's bare feet into extended contact with the grounded plane by conductively coupling the bare feet with the conductive pad;
    conducting a mobile surface charge of free electrons from the earth to the body; and
    reducing the oxidative state of residual immune response free radicals in the body using free electrons provided through contact with the grounded plane.

18. The process of claim 17, wherein the conducting step includes the step of restoring the body's natural supply of free electrons and reducing residual immune response reactive oxygen species free radicals in the body.

19. The process of claim 10, wherein the reducing step includes the steps of speeding recovery of the body from acute injury, inhibiting expression of chronic inflammation in the body, and inhibiting free radical oxidation of healthy tissue in the body.

* * * * *